United States Patent [19]
Okami et al.

[11] Patent Number: 4,795,743
[45] Date of Patent: Jan. 3, 1989

[54] 2'-DEAMINO-2'-HYDROXYISTAMYCIN $B_o$ DERIVATIVES OF LOW TOXICITY

[75] Inventors: Yoshiro Okami, Tokyo; Shinichi Kondo, Kanagawa; Daishiro Ikeda, Tokyo; Hamao Umezawa, deceased, late of Tokyo, all of Japan, by Mieko Umezawa, Kazuo Umezawa, Yoji Umezawa, heirs

[73] Assignee: Zaidan Hojin Biseibutsu Kagaku Kenkyu Kai, Japan

[21] Appl. No.: 21,781

[22] Filed: Mar. 4, 1987

[30] Foreign Application Priority Data

Mar. 11, 1986 [JP] Japan .................................. 61-51557

[51] Int. Cl.$^4$ ........................ A61K 31/70; C07H 15/22
[52] U.S. Cl. ..................................... 514/36; 536/16.1; 536/16.8
[58] Field of Search .................... 536/16.1, 16.8, 17.2, 536/17.9; 514/25, 36

[56] References Cited

U.S. PATENT DOCUMENTS 4,296,106 10/1981 Umezawa et al. ................. 536/16.8
4,472,388 9/1984 Umezawa et al. ................. 536/16.8

FOREIGN PATENT DOCUMENTS 0096392 12/1983 European Pat. Off. .

Primary Examiner—J. R. Brown
Assistant Examiner—Elli Peselev
Attorney, Agent, or Firm—Lalos & Keegan

[57] ABSTRACT

As new 2'-deamino-2'-hydroxyistamycin $B_o$ derivatives are provided four compounds, namely 2'-deamino-2'-hydroxyistamycin B; 2'-deamino-2'-hydroxy-3-O-demethylistamycin B; 4-N-($\beta$-alanyl)-2'-deamino-2'-hydroxyistamycin $B_o$; and 4-N-($\beta$-alanyl)-2'-deamino-2'-hydroxy-3-O-demethylistamycin $B_o$ which all exhibit high antibacterial activity and low acute toxicity in combination. These new compounds are useful as antibacterial agent.

8 Claims, No Drawings

2'-DEAMINO-2'-HYDROXYISTAMYCIN $B_o$ DERIVATIVES OF LOW TOXICITY

SUMMARY OF THE INVENTION

This invention relates to 2'-deamino-2'-hydroxyistamycin $B_o$ derivatives which are each a new compound useful as semi-synthetic aminoglycosidic antibiotics having antibacterial activity and low toxicity in combination. This invention also relates to the production and uses of these new compounds.

BACKGROUND OF THE INVENTION

We, the present inventors, already provided istamycins A, B, $A_o$ and $B_o$ as the aminoglycosidic antibiotics which are produced by a microorganism, *Streptomyces tenjimariensis* of the actinomycetes (Japanese patent application first publication "Kokai" Nos. 14569/80 and 43295/81; U.S. Pat. No. 4,296,106; U.K. Pat. No. 2,048,855B); istamycins C and $C_o$ (Japanese patent application first publication "Kokai" No. 118598/82); istamycins $A_1$, $B_1$, $C_1$ and $A_2$ (Japanese patent application first publication "Kokai" No. 139092/82); and 2''-N-formimidoylistamycins A and B (Japanese patent application No. 80218/82; Japanese patent application first publication "Kokai" No. 198298/83; U.S. Pat. No. 4,382,926; U.K. Pat. No. 2,088,851B). Amongst these istamycins, istamycin B is of the highest antibacterial activity. We have further studied istamycin B to produce some derivatives therefrom, and succeeded to synthesize 3-O-demethylistamycin B which is active against resistant bacteria, *Pseudomonas aeruginosa* and also against a variety of resistant strains of gram-negative and gram-positive bacteria (Japanese patent application first publication "Kokai" No. 50996/82; U.S. Pat. No.4,499,083; European Pat. No. 0048549). Although the various derivatives of istamycin B which were already provided by us are useful as antibacterial agent, they are not necessarily an antibacterial agent which is satisfactory completely, and they are reported to have inneligible acute toxicity. In these circumstances, it is still demanded to provide any new derivatives of istamycin B which show lowered acute toxicity with maintaining the high antibacterial activity of the parent istamycin B.

DETAILED DESCRIPTION OF THE INVENTION

Therefore, we have continued our study in an attempt to provide any more useful and new derivatives of istamycin B. As a result, we have now succeeded in synthesizing four derivatives of 2'-deamino-2'-hydroxyistamycin $B_o$, as new compounds, and found that these four new compounds now synthesized have useful antibacterial activity and low toxicity. Amongst these four new compounds, 4-N-($\beta$-alanyl)-2'-deamino-2'-hydroxy-3-O-demethylistamycin $B_o$ has antibacterial activity as high as that of istamycin B and shows a lower toxicity than itstamycin B. Based on these findings, we have completed this invention.

According to an aspect of this invention, therefore, there is provided as new compound a 2'-deamino-2'-hydroxyistamycin $B_o$ derivative represented by the general formula (I)

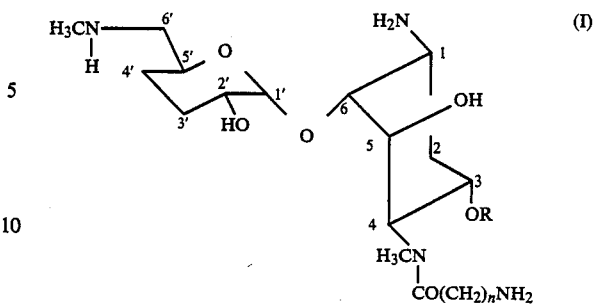

wherein R is a methyl group or a hydrogen atom and n is an integer of 1 or 2, or a pharmaceutically acceptable acid addition salt thereof.

Particular examples of the compound of the formula (I) according to this invention includes the following four compounds:

(1) 2'-Deamino-2'-hydroxyistamycin B, that is, the compound of the general formula (I) where R is methyl ($CH_3$) and n is 1 (this compound is hereinafter referred to as Compound No. 1):

(2) 2'-Deamino-2'-hydroxy-3-O-demethylistamycin B, that is, the compound of the general formula (I) where R is a hydrogen atom (H) and n is 1 (this compound is hereinafter referred to as Compound No. 2);

(3) 4-N-($\beta$-Alanyl)-2'-deamino-2'-hydroxyistamycin $B_o$, namely the compound of the general formula (I) where R is methyl ($CH_3$) and n is 2 (this compound is referred to as Compound No. 3); and (4) 4-N-($\beta$-Alanyl)-2'-deamino-2'-hydroxy-3-O-demethylistamycin $B_o$, namely the compound of the general formula (I) where R is a hydrogen atom (H) and n is 2 (this compound is referred to as Compound No. 4); as well as pharmaceutically acceptable acid addition salts of these particular compounds.

These new derivatives show the physico-chemical properties and biological properties described below.

Compound No. 1 of this invention (as the free base) is in the form of colorless and hygroscopic powder of which the melting point cannot be measured definitely. It shows a specific optical rotation $[\alpha]_D^{28} + 108.8°$ (c 1, water) and has a molecular formula $C_{17}H_{34}N_4O_6$ in view of that the mass spectrometry gave m/z 391 (SIMS, MH+).

Compound No. 2 of this invention (as the free base) is also in the form of a colorless and hygroscopic powder of which the melting point cannot be measured definitely. It shows a specific optical rotation $[\alpha]_D^{23} + 109.4°$ (c 1, water) and has a molecular formula $C_{16}H_{32}N_4O_6$ in view of that the mass spectrometry gave m/z 377 (SIMS, MH+).

Compound No. 3 of this invention (as the free base) is in the form of a colorless and hydroscopic powder of which the melting point cannot be measured definitely, too. It shows a specific optical rotation $[\alpha]_D^{25} + 119.6°$ (c 1, water) and has a molecular formula $C_{18}H_{36}N_4O_6$ in view of that the mass spectrometry gave m/z 405 (SIMS, MH+).

Compound No. 4 of this invention (as the free base) is in the form of a colorless and hygroscopic powder of which the melting point cannot be measured definitely. It shows a specific optical rotation $[\alpha]^{23}_D + 109.4°$ (c 1, water) and has a molecular formula $C_{17}H_{34}N_4O_6$ in view of that the mass spectrometry gave m/z 391 (SIMS, MH+).

Compounds Nos. 1, 2, 3 and 4 of this invention have a mobility of 1.73, 1.74, 1.84 and 1.85, respectively in a high voltage paper electrophoresis (3,500 Volts, 5 minutes) using formic acid-acetic acid-water (25:75:900 by volume), assumed that the mobility of alanine is then 1.0.

Antibacterial spectra of Compound Nos. 1, 2, 3 and 4 according to this invention are shown in Table 1 below, in comparison with that of istamycin B. The minimum inhibitory concentrations (mcg/ml) of these compounds against the growth of test microorganisms were determined according to a standard serial dilution method of Japan Society of Chemotherapy using Müller-Hinton medium as the incubation medium at 37° C. after incubation for 18 hours. From the results of Table 1, it is revealed that the new compounds of this invention exhibit broad and excellent antibacterial activities against a wide variety of gram-negative and gram-positive bacteria, including test strains which are resistant to different aminoglycosidic antibiotics. In particular, it has been confirmed that Compound No. 4 of this invention exhibits very much good antibacterial activity against the tested bacterial species, including *Pseudomonas aeruginosa*.

TABLE 1

| Test Organisms | Minimum Growth Inhibitory Concentration (mgc/ml) | | | | |
|---|---|---|---|---|---|
| | Compound No. 1 | Compound No. 2 | Compound No. 3 | Compound No. 4 | Istamycin B (comparative) |
| Staphylococcus aureus 209P | 3.13 | 3.13 | 6.25 | 1.56 | 0.78 |
| Staphylococcus aureus Smith | 3.13 | 1.56 | 3.13 | 1.56 | 0.39 |
| Staphylococcus aureus Ap 01 | 6.25 | 6.25 | 6.25 | 3.13 | 1.56 |
| Staphylococcus epidermidis 109 | 6.25 | 1.56 | 3.13 | 1.56 | 0.78 |
| Micrococcus flavus FDA 16 | 25 | 12.5 | 6.25 | 3.13 | 25 |
| Sarcina lutea PCI 1001 | 3.13 | 1.56 | 3.13 | 1.56 | 0.39 |
| Bacillus anthracis | 12.5 | 1.56 | 1.56 | 1.56 | 0.78 |
| Bacillus subtilis PCI 219 | 3.13 | 3.13 | 6.25 | 3.13 | 0.78 |
| Bacillus subtilis NRRL B-558 | 3.13 | 3.13 | 3.13 | 0.78 | 0.78 |
| Bacillus cereus ATCC 1-702 | 50 | 6.25 | 25 | 6.25 | 6.25 |
| Corynebacterium bovis 1810 | 3.13 | 3.13 | 12.5 | 3.13 | 0.78 |
| Mycobacterium smegmatis ATCC 607 | 25 | 6.25 | 25 | 6.25 | 0.78 |
| Escherichia coli NIHJ | 1.56 | 1.56 | 1.56 | 1.56 | 0.78 |
| Escherichia coli K-12 | 3.13 | 1.56 | 3.13 | 1.56 | 0.78 |
| Escherichia coli K-12 R5 | 3.13 | 3.13 | 3.13 | 1.56 | 0.78 |
| Escherichia coli K-12 R388 | 3.13 | 3.13 | 3.13 | 1.56 | 1.56 |
| Escherichia coli K-12 J5 R11-2 | 1.56 | 1.56 | 3.13 | 0.78 | 0.78 |
| Escherichia coli K-12 ML1629 | 6.25 | 6.25 | 6.25 | 3.13 | 1.56 |
| Escherichia coli K-12 ML1630 | 6.25 | 6.25 | 12.5 | 6.25 | 6.25 |
| Escherichia coli K-12 ML1410 | 6.25 | 6.25 | 12.5 | 6.25 | 3.13 |
| Escherichia coli K-12 ML1410 R81 | 6.25 | 6.25 | 25 | 6.25 | 1.56 |
| Escherichia coli K-12 LA290 R55 | 6.25 | 6.25 | 12.5 | 6.25 | 3.13 |
| Escherichia coli K-12 LA290 R56 | 3.13 | 3.13 | 3.13 | 3.13 | 0.78 |
| Escherichia coli K-12 LA290 R64 | 3.13 | 3.13 | 3.13 | 1.56 | 1.56 |
| Escherichia coli W677 | 1.56 | 3.13 | 3.13 | 1.56 | 0.78 |
| Escherichia coli JR66/W677 | 3.13 | 6.25 | 6.25 | 3.13 | 1.56 |
| Escherichia coli K-12 C600 R135 | 3.13 | 3.13 | 3.13 | 3.13 | 12.5 |
| Escherichia coli JR225 | 3.13 | 1.56 | 3.13 | 1.56 | 0.78 |
| Klebsiella Pneumoniae PCI 602 | 6.25 | 6.25 | 12.5 | 3.13 | 1.56 |
| Klebsiella pneumoniae 22 = 3038 | 12.5 | 6.25 | 12.5 | 3.13 | 3.13 |
| Shigella dysernteriae JS11910 | 6.25 | 12.5 | 3.13 | 3.13 | 3.13 |
| Shibella flexneri 4b JS11811 | 12.5 | 12.5 | 6.25 | 6.25 | 3.13 |
| Shigella sonnei | 6.25 | 6.25 | 6.25 | 3.13 | 3.13 |
| Salmonella typhi T-63 | 1.56 | 0.78 | 1.56 | 0.78 | 0.39 |
| Salmonella enteritidis 1891 | 6.25 | 12.5 | 6.25 | 3.13 | 3.13 |
| Proteus vulgaris OX19 | 3.13 | 1.56 | 3.13 | 1.56 | 0.78 |
| Proteus rettgeri GN311 | 6.25 | 1.56 | 3.13 | 0.78 | 1.56 |
| Proteus rettgeri GN466 | 3.13 | 1.56 | 0.78 | 0.39 | 0.78 |
| Serratia marcescens | 12.5 | 12.5 | 6.25 | 3.13 | 6.25 |
| Serratia sp. SOU | 6.25 | 3.13 | 3.13 | 1.56 | 25 |
| Serratia sp. 4 | >100 | .25 | 100 | 12.5 | 50 |
| Providencia sp. Pv16 | 6.25 | 3.13 | 3.13 | 1.56 | 1.56 |
| Providencia sp. 2991 | 12.5 | 6.25 | 12.5 | 3.13 | 3.13 |
| Pseudomonas aeruginosa A3 | 6.25 | 0.39 | 3.13 | 0.39 | 0.39 |
| Pseudomonas aeruginosa No.12 | 100 | 25 | 100 | 12.5 | 25 |
| Pseudomonas aeruginosa H9 | >100 | 12.5 | 50 | 12.5 | 12.5 |
| Pseudomonas aeruginosa H11 | >100 | 25 | 100 | 12.5 | 50 |
| Pseudomonas aeruginosa TI-13 | 100 | 12.5 | 100 | 12.5 | 25 |
| Pseudomonas aeruginosa GN315 | 100 | 12.5 | 50 | 12.5 | 25 |
| Pseudomonas aeruginosa 99 | >100 | 50 | >100 | 25 | >100 |
| Pseudomonas aeruginosa B-13 | >100 | 25 | 100 | 12.5 | >100 |
| Pseudomonas aeruginosa 21-75 | >100 | 25 | 100 | 12.5 | 50 |
| Pseudomonas aeruginosa PST1 | 100 | 25 | 100 | 12.5 | 50 |
| Pseudomonas aeruginosa ROS 134/PU21 | >100 | 50 | >100 | 100 | >100 |
| Pseudomonas | >100 | 12.5 | 50 | 25 | 25 |

TABLE 1-continued

| | Minimum Growth Inhibitory Concentration (mgc/ml) | | | | |
|---|---|---|---|---|---|
| Test Organisms | Compound No. 1 | Compound No. 2 | Compound No. 3 | Compound No. 4 | Istamycin B (comparative) |
| aeruguinosa K-Ps 102 | | | | | |
| Pseudomonas maltophilia GN907 | >100 | >100 | >100 | >100 | >100 |

In the test of acute toxicity by intravenous injection in mice, it has been found that all of the mice receiving Compound No. 1, No. 2, No. 3 or No. 4 of this invention at dosage of 200 mg/kg survived without showing any sympton of toxicity, revealing the low toxicity of the new compounds of this invention.

Compound Nos. 1, 2, 3 and 4 of this invention are each obtainable in the form of the free base, a hydrate or a carbonate thereof and may be converted into a pharmaceutically acceptable acid addition salt thereof in a known manner by reacting with a pharmaceutically acceptable acid. The acid addition salt of the compound of this invention is preferred in view of its improved stability. The acid to be added for formation of the acid addition salt includes a pharmaceutically acceptable inorganic acid such as carbonic acid, hydrochloric acid, hydrobromic acid, sulfuric acid, phosphoric acid and nitric acid; and a pharmaceutically acceptable organic acid such as acetic acid, malic acid, citric acid, ascorbic acid and methanesulfonic acid.

The new compound of this invention represented by the general formula (I)

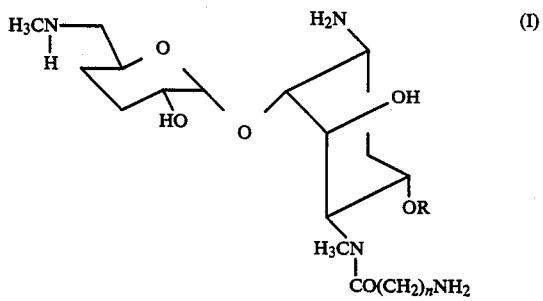

wherein R and n are as defined above, including Compound No. 1 according to the formula (I) were $R=CH_3$, $n=1$; Compound No. 2 according to the formula (I) where $R=H$, $n=1$, Compound No. 3 according to the formula (I) were $R=CH_3$, $n=2$, and Compound No. 4 according to the formula (I) where $R=H$, $n=2$, may be produced by using istamycin $B_o$ or 3-O-demethylistamycin $B_o$ of the formula (II)

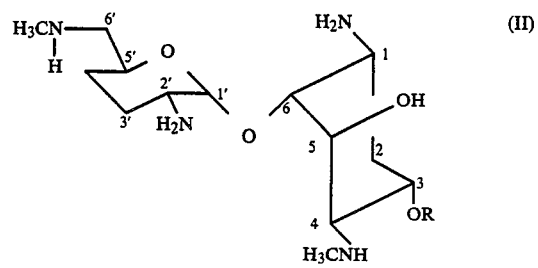

wherein R is methyl for istamycin $B_o$ and R is hydrogen atom for 3-O-demethylistamycin $B_o$ (see Japanese patent application first publication "Kokai" Nos. 43295/81 and 50996/82; U.S. Pat. No. 4,499,083 and European Pat. No. 0048549) as a starting compound and removing the 2'-amino group therefrom and instead thereof introducing a 2'-hydroxy group, followed by acylating the 4-methylamino group with glycine or β-alanine.

The starting compound available for this purpose may suitably be an appropriate amino-protected derivative of istamycin $B_o$ or 3-O-demethylistamycin $B_o$ represented by the general formula (III)

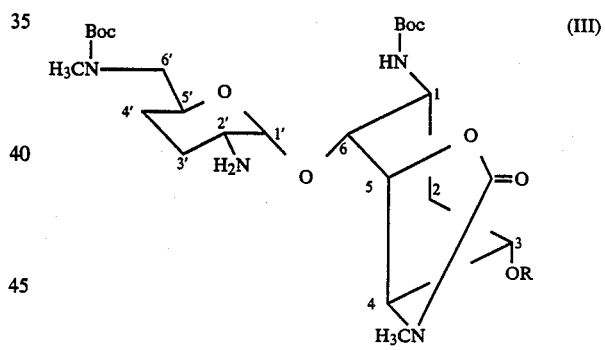

wherein Boc denotes a t-butoxycarbonyl group $(CH_3)_3COCO-$ and R denotes a methyl group ($-CH_3$) or a hydrogen atom (H), such as 1,6'-di-N-Boc-istamycin $B_o$-4,5-N,O-carbamate [the compound of formula (III) where R is methyl] and 1,6'-di-N-Boc-3-O-demethylistamycin $B_o$-4,5-N,O-carbamate [the compound of formula (III) where R is hydrogen]. For the replacement of the 2'-amino group by the 2'-hydroxy group in the starting compound of the formula (III), a conventional reaction for the deamination may be effected at first, for example, by oxidising the 2'-amino group with 3,5-di-t-butyl-o-benzoquinone to give a corresponding 2'-keto derivative of the compound (III) represented by the formula (VI)

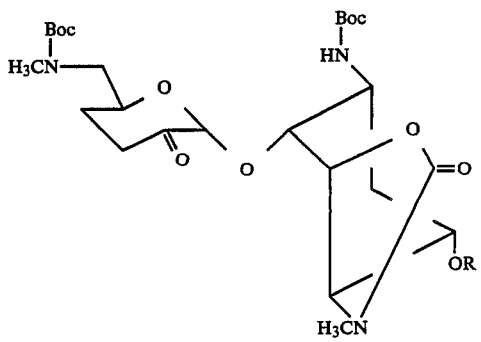

(VI)

wherein Boc and R are defined above. Subsequently the 2'-keto group of the compound of the formula (VI) may be reduced by reacting with a metal hydride such as sodium borohydride so that an equatorial hydroxy group is readily introduced in the 2'-position in a high yield, affording a compound of the general formula (IV)

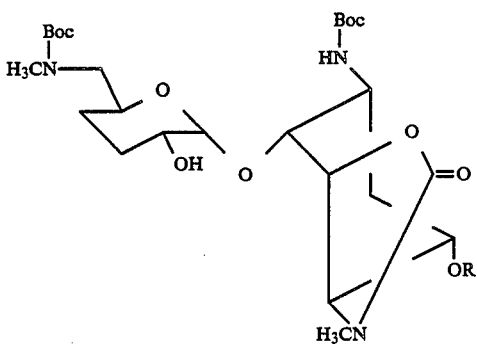

(VI)

wherein Boc and R have the same meanings as defined in the formula (III), such as 1,6'-di-N-Boc-2'-deamino-2'-hydroxyistamycin $B_o$-4,5-carbamate [the compound of formula (IV) where R is methyl] and 1,6'-di-N-Boc-2'-deamino-2'-hydroxy-3-O-demethylistamycin $B_o$-4,5-carbamate [the compound of formula (IV) where R is hydrogen].

The compound of formula (IV) may further be hydrolyzed with alkali to fission the ring of the 4,5-carbamate moiety of the compound (IV) for the deprotection purpose and give a compound of the general formula (V)

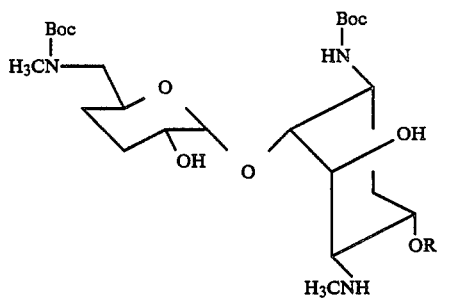

(V)

wherein R is as defined above, such as 1,6'-di-N-Boc-2'-deamino-2'-hydroxyistamycin $B_o$ [the compound of formula (V) where R is methyl] and 1,6-di-N-Boc-2'-deamino-2'-hydroxy-3-O-demethylistamycin $B_o$ [the compound of formula (V) where R is hydrogen]. In a next step, the 4-methylamino group of the compound of formula (V) is acylated with glycine or β-alanine or an amino-protected derivative thereof in a known manner, for example, according to the method as described in the aforesaid Japanese patent application first publication "Kokai" No. 50996/82 or U.S. Pat. No. 4,499,083 to produce an acylation product of the formula (VII)

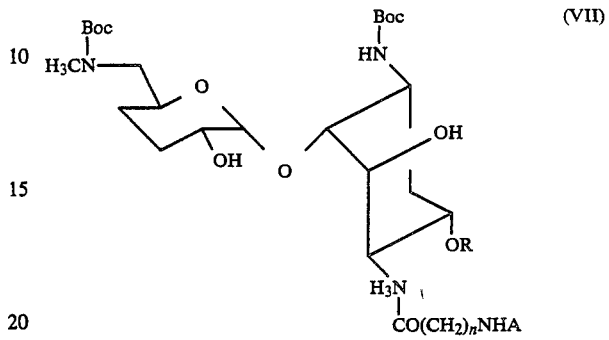

(VII)

wherein Boc and R are as defined above and A is a hydrogen atom or an amino-protecting group coming from the amino-protected glycine or β-alanine derivative when employed. When the acylation product of formula (VII) is then treated in a known manner according to the conventional deprotecting technique to remove the remaining amino-protecting group (Boc and A) therefrom, there is produced the desired compound of the general formula (I) according to this invention, such as Compound No. 1, 2, 3 or 4 of this invention.

As already described, the new compound (I) of this invention possesses a high antibacterial activity against a wide variety of bacteria. Further, the compound has a low toxicity to animals as shown by the results that mice tolerated intravenous administration of 200 mg/Kg of the compound. Thus, the compound is very useful as an antibacterial agent and for this purpose it is generally formulated into the form of pharmaceutical composition, which may be administered into man or an animal in a way known per se.

Accordingly, this invention also provides a pharmaceutical composition comprising a therapeutically or bactericidally effective amount of the compound of above formula (I) or a pharmaceutically acceptable acid addition salt thereof, as the active ingredient, in combination with a pharmaceutically acceptable carrier or adjuvant. This invention further provides a method of inhibiting the bacterial growth in an animal which comprises administering a therapeutically or bactericidally effective amount of the compound (I) or a pharmaceutically acceptable salt thereof to an animal infected with or susceptible to bacteria. It will be appreciated that an appropriate amount of the effectiv ingredient to be administered for the envisaged purpose will vary depending upon the particular composition formulated, the mode of administration, the conditions to be treated and the nature of the bacteria to be controlled thereby. By way of general guidance, the effective ingredient will be administered into an animal at a dosage of 0.5-10 mg per kg of the animal body.

This invention is further illustrated but not limited by the following Example.

EXAMPLE 1

Production of Compound No. 1 of this invention (a) Istamycin B₀ (the free base, 2.4 g; 7.25 mmol) was mixed with a solution of zinc acetate dihydrate [Zn(COCH₃)₂.2H₂O] (3.6 g; 16.4 mmol) in 60 ml of methanol, and the resultant mixture was stirred at room temperature for 5 hours. The solution obtained was admixed with 14.7 g (59.7 mmol) of 2 (t-butoxycarbonyloxyimino)-2-phenylacetonitril (known as Boc-ON reagent for introduction of the t-butoxycarbonyl group (Boc-) as an amino-protecting group; a product of Aldorich Co., U.S.A.), followed by effecting the reaction at room temperature overnight (for the reaction of introduction of the amino-protecting Boc group). The reaction solution was then mixed with 5 ml of an concentrated aqueous ammonium hydroxide (NH₄OH) and then stirred for 30 minutes. The resulting solution was then concentrated under reduced pressure and the residue was dissolved in 100 ml of chloroform. The solution obtained was washed with 1 N aqueous ammonium hydroxide and then with water. The solution was subsequently dried over anhydrous sodium sulfate and filtered, and the filtrate was concentrated under reduced pressure. The solid residue obtained was subjected to column chromatography on a column of Wako-Gel C-200 (300 g) developed with a mixed solvent of chloroform-methanol (10:1) as eluent. Thus, the 1,2',6'-tri-N-Boc derivative of istamycin B₀, that is, 1,2',6'-tri-N-t-butoxycarbonylistamycin B₀ (2.9 g) was obtained. Yield 63%.

(b) The 1,2',6'-tri-N-Boc derivative of istamycin B₀ (2.8 g; 4.6 mmol) obtained as above was dissolved in 60 ml of dry toluene and the resulting solution was admixed with 740 mg (4.6 mmol) of carbonyldiimidazole, followed by effecting the reaction at 60° C. for 1 hour (for the formation of the 4,5-carbamate ring to protect the 4-methylamino group and 2-hydroxy group). The reaction solution obtained was mixed with 40 ml of toluene and washed with water, and the toluene was distilled off from the solution to leave 3.0 g (quantitative yield) of 1,2',6'-tri-N-Boc-istamycin B₀-4,5-carbamate represented by formula (III')

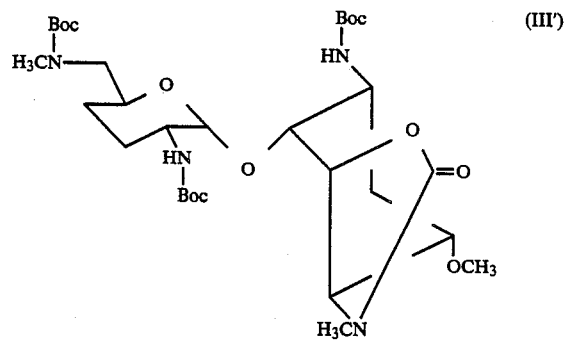

wherein Boc denotes t-butoxycarbonyl group.

(c) The 1,2',6'-tri-N-Boc-istamycin B₀-4,5-carbamate (2.82 g; 4.281 mmol) obtained as above was taken up into 20 ml of 90% aqueous trifluoroacetic acid and the solution was allowed to stand at room temperature for 1 hour to effect the reaction of removing the Boc group and produce istamycin B₀-4,5-carbamate. The resulting reaction solution was concentrated to dryness and the residue was dissolved in 100 ml of water, to which was then added 1N aqueous NH₄OH to adjust the pH to 6–7. The aqueous solution so neutralized was then subjected to column chromatography on a column of 500 ml of Amberlite CG-50 (NH₄⁺-form) and the resin column was then washed with water and eluted with 0.3N aqueous NH₄OH. The active fractions of the eluate containing the desired compound were collected together and concentrated to dryness to afford 1.35 g (yield 88.0%) of the istamycin B₀-4,5-carbamate of the formula

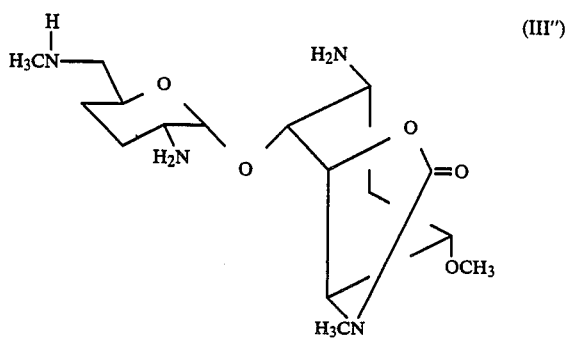

$[\alpha]_D^{23} + 110.7°$ (c 1, water).

(d) To a solution of the istamycin B₀-4,5-carbamate of the formula (III'') (1.35 g; 3.766 mmol) in methanol (60 ml) was added 1.86 g of the Boc-ON reagent, and the resulting mixture was stirred at room temperature for 3 hours to effect the reaction for introduction of the t-butoxycarbonyl group (Boc). The reaction solution obtained was admixed with 1 ml of a concentrated aqueous ammonium hydroxide and then further stirred for 30 minutes. The reaction solution was subsequently concentrated and the residue was dissolved in 100 ml of chloroform. The solution in chloroform was washed with 50 ml of water (H₂O) and dried over anhydrous sodium sulfate. The dried solution was filtered and concentrated, and the residue was chromatographed on a column of silica gel (200 g) developed with chloroform-methanol (30:1) as eluent, to give 322 mg (15.3%) of the desired 1,6'-di-N-Boc-istamycin B₀-4,5-carbamate of the formula (III''')

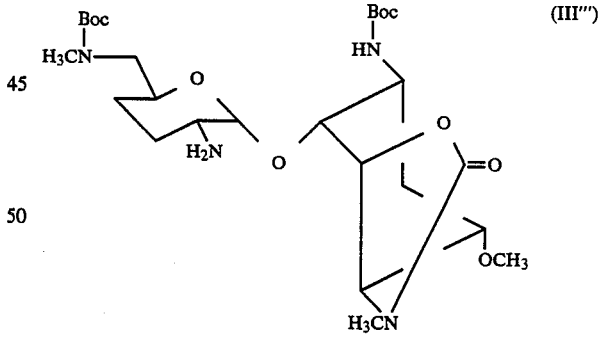

wherein Boc denotes t-butoxycarbonyl group. $[\alpha]_D^{27} + 76.9°$ (c 1, CHCl₃).

(e) To a solution of 254 mg (0.455 mmol) of the 1,6-di-N-Boc-istamycin B₀-4,5-carbamate of the formula (III''') obtained as above in 15 ml of methanol was added 400 mg (1.816 mmol) of 3,5-di-t-butyl-o-benzoquinone (as a mild oxidizing agent), and the mixture obtained was stirred at 50° C. for 1 hour to effect the oxidation of the 2-amino group of the compound (III'''). To the resultant reaction solution was added 5 ml of 1M aqueous oxalic acid, followed by stirring the mixture at 50° C. for 4 hours to complete the reaction. The reaction solution obtained was neutralized by addition of powdered sodium hydrogen carbonate (NaHCO$_3$) and then concentrated to dryness. The residue was dissolved in 30 ml of chloroform and the solution in chloroform was washed with water (10 ml×3), dried over anhydrous sodium sulfate, filtered and concentrated. The residue obtained was then chromatographed on a column of silica gel (25 g) developed with 50 ml of chloroform and then with chloroform-methanol (40:1). Thus, the desired 2'-deamino-2'-keto 1,6'-di-N-Boc-istamycin B$_o$-4,5-carbamate of the formula

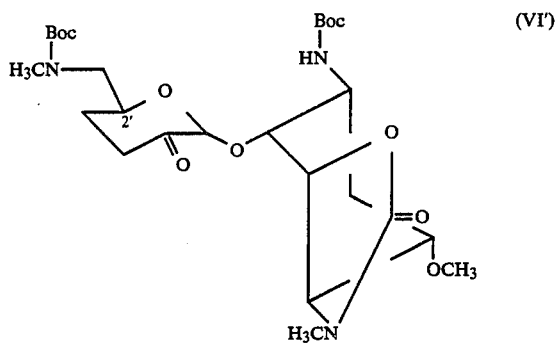

wherein Boc is as defined above, in a yield of 163.2 mg (64.4%).

(f) The 2'-keto-istamycin B$_o$ derivative of the formula (VI') above (157 mg; 0.282 mmol) was dissolved in 15 ml of methanol, and to this methanolic solution was added 20 mg (0.529 mmol) of sodium borohydride (NaBH$_4$) under ice-cooling. The resulting mixture was stirred for 30 minutes under ice cooling and then treated by passing therethrough a stream of CO$_2$ gas to consume up the excess of sodium borohydride. The treated mixture was concentrated to dryness and the residue was taken up in 30 ml of chloroform. The solution in chloroform was washed with water (10 ml×3), dried over anhydrous sodium sulfate, filtered and concentrated. The residue obtained was chromatographed on a column of silica gel (15 g) developed with chloroform-methanol (30:1) as eluent, to produce the desired 2'-deamino-2'-hydroxy-1,6'-di-N-t-butoxycarbonyl-istamycin B$_o$-4,5-carbamate of the formula

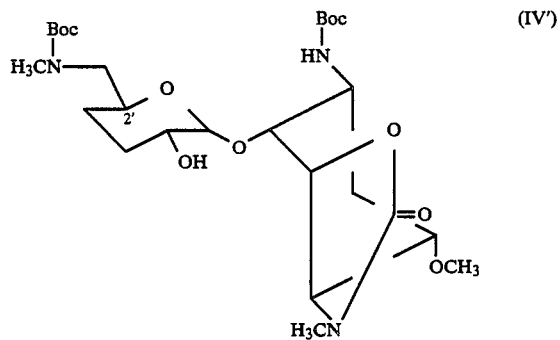

wherein Boc is as defined above, in a yield of 140.8 mg (89.3%). $[\alpha]_D^{28}+68.8°$ (c 1 CHCl$_3$), SIMS: 560 (MH+).

The product of the formula (IV') so obtained was analyzed by a thin layer chromatography (TLC), when it was not detected that the 2'-hydroxy-istamycin B$_o$ derivative of the formula (IV') as produced contained the 2'-epimer.

(g) To a solution of 135 mg (0.241 mmol) of the 2'-hydroxy-istamycin B$_o$ derivative of the formula (IV') in 10 ml of aqueous 50% dioxane was added 304 mg (0.964 mmol) of barium hydroxide [Ba(OH)$_2$.2.8H$_2$O]. The mixture obtained was stirred at 70° C. for 6 hours to effect the hydrolytic ring-fission of the 4,5-carbamate ring of the compound (IV'). The reaction solution was neutralized by passing a stream of CO$_2$ gas therethrough, and the neutralized solution was filtered and the filtrate was concentrated to dryness. The residue obtained was dissolved in 30 ml of chloroform. The solution in chloroform was washed with water (10 ml×3), dried over anhydrous sodium sulfate, filtered and concentrated to dryness. The residue was then dissolved in chloroform and the solution was subjected to chromatography on a column of silica gel (10 g) developed with chloroform-methanol (3:1). Just after the desired product begun to appear in some fractions of the eluate, the silica gel column was developed with chloroform-methanol-conc. NH$_4$OH (30:30:1). Subsequently, the fractions of the eluate containing the desired product was collected together and concentrated to dryness to afford the desired 1,6-di-N-Boc-2'-deamino-2'-hydroxyistamycin B$_o$ of the formula

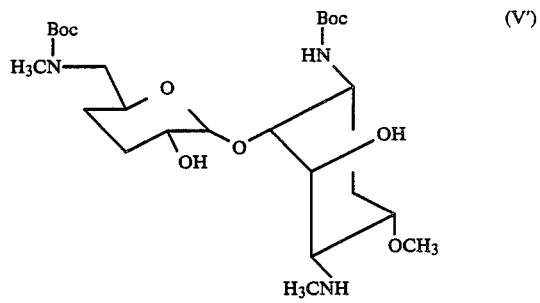

wherein Boc is as defined above, in a yield of 110.5 mg (85.9%). $[\alpha]_D^{28}+82.2°$ (c 1, CHCl$_3$), SIMS: 534(MH+).

(h) The compound of the formula (V') obtained (24.5 mg; 0.0459 mmol) was dissolved in 1 ml of dioxane, and to the resultant solution were added 18.7 mg (0.0687 mmol) of N-hydroxysuccinimide ester of N-t-butoxycarbonylglycine and 10 μl (0.0717 mmol) of triethylamine, and the resulting mixture was stirred at 60° C. for 1 hour to acylate the 4-methylamino group with the glycine compound. The reaction solution was admixed with 0.1 ml of 1N aqueous NH$_4$OH and stirred at room temperature for 10 minutes, and then the reaction solution was concentrated to dryness. The residue was dissolved in 30 ml of chloroform and the solution was washed with water (10 ml×3), dried over anhydrous sodium sulfate, filtered and concentrated. The residue obtained was chromatographed on a column of silica gel (3 g) developed with chloroform-methanol (50:1) to give 29.5 mg (93.0%) of the desired 1,6',2''-tri-N-Boc-2'-deamino-2'-hydroxyistamycin B of the formula (Ia)

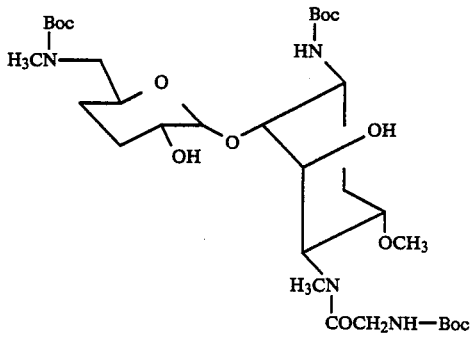

(Ia)

wherein Boc is as defined above. $[\alpha]_D^{28}+66.7°$ (c 1, CHCl₃), SIMS: 691 (MH+).

(i) The 1,6′,2″-tri-N-Boc-2′-deamino-2′-hydroxyistamycin B of the formula (Ia) (29.5 mg; 0.0472 mmol) obtained was mixed with 90% aqueous trifluoroacetic acid and the mixture was allowed to stand at room temperature for 1 hour to effect the hydrolytic removal of the t-butoxycarbonyl group (Boc). The reaction solution obtained was concentrated to dryness, and the residue was dissolved in 3 ml of water. The resultant aqueous solution was adjusted to pH 6–7 by addition of 1N aqueous NH₄OH and then passed into a column of 3 ml of Amberlite CG-50 (NH₄+-form) to make the adsorption of the compound of the formula (Ia) by the resin. The resin column was washed successively with 10 ml of water, 10 ml of 0.1N aqueous NH₄OH and 10 ml of 0.2N aqueous NH₄OH and then developed with 0.3N aqueous NH₄OH. The fractions of the eluate containing the compound (Ia) were collected together and concentrated to dryness to obtain the desired Compound No. 1 of this invention, that is, 2′-deamino-2′-hydroxyistamycin B in a yield of 15.3 mg (91.8%). $[\alpha]_D^{28}+108.8°$ (c 1, water).

EXAMPLE 2

Production of Compound No. 2 of this invention (a) 3-O-demethylistamycin B₀ (510 mg; 1.68 mmol) was dissolved in 20 ml of methanol, and to the resulting solution was added 680 mg (272 mmol) of nickel acetate tetra-hydrate [Ni(COCH₂)₂.4H₂O]. The mixture obtained was stirred at room temperature for 4.5 hours and then admixed with 1.34 g (5.45 mmol) of said Boc-ON reagent, followed by agitation at room temperature overnight, to effect the reaction of introducing the t-butoxycarbonyl group into the amino groups of the 3-O-demethylistamycin B₀. The reaction solution was admixed with 2 ml of a concentrated aqueous NH₄OH, stirred for 30 minutes and then concentrated under reduced pressure. The residue was dissolved in 40 ml of chloroform and the solution was washed three times with 1N aqueous NH₄OH and once with water, dried over anhydrous sodium sulfate (Na₂SO₄) and concentrated under reduced pressure by distilling off the chloroform.

The residue was chromatographed on a column of Wako-Gel C-200 (100 g) developed with chloroform-methanol-17% aqueous ammonia (80:10:1) as eluent, and there was obtained a colorless solid of 1,2′,6′-tri-N-Boc-3-O-demethylistamycin B₀ in a yield of 890 mg (86%).

(b) The tri N-Boc-3-O-demethylistamycin B₀ (560 mg; 0.906 mmol) obtained was dissolved b 86%).

(b) The tri N-Boc-3-O-demethylistamycin B₀ (560 mg; 0.906 mmol) obtained was dissolved in 10 ml of anhydrous toluene, to which was added 162 mg (0.997 mmol) of carbonyldiimidazole. The resultant mixture was stirred at 60° C. for 2.5 hours to effect the reaction of producing the corresponding 4,5-carbamate derivative. The reaction solution was then admixed with 20 ml of toluene, washed twice with 1N aqueous NH₄OH and once with water, dried over anhydrous Na₂SO₄ and then concentrated under reduced pressure. The residue was chromatographed on a column of Wako-Gel C-200 (80 g) developed with toluene-ethyl acetate (1:10) as eluent, to afford 472 mg of a colorless solid of 1,2′,6′-tri-N-Boc-3-O-demethylistamycin B₀-4,5-carbamate. Yield 81%. IR: 1755 cm⁻¹ (attributable to the 5-membered carbamate).

(c) The tri-N-Boc-3-O-demethylistamycin B₀-4,5carbamate (358 mg; 0.555 mmol) obtained was mixed with 5 ml of 90% aqueous trifluoroacetic acid, and the mixture was allowed to stand at room temperature for 1 hour to effect the removal of the Boc groups. Thereafter, the reaction solution was concentrated to dryness. The residue was taken up into 20 ml of water and, after adjustment to pH 6–7 by addition of 1N aqueous NH₄OH, the resulting aqueous solution was passed into a column 20 ml of Amberlite CG-50 (NH₄+-form) for chromatography. The resin column was washed with 60 ml of water and then eluted with 0.3N aqueous NH₄OH, and the fractions of the eluate containing the desired product were combined together and concentrated to dryness, affording 174 mg (91.0%) of the 3-O-demethylistamycin B₀-4,5-carbamate of the formula

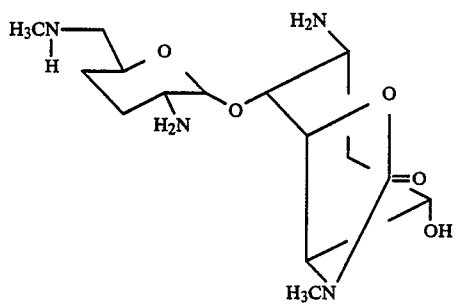

$[\alpha]_D^{22}+113.6°$ (c 1, water). (d) The 4,5-carbamate derivative of the above formula obtained (174 mg; 0.505 mmol) was dissolved in 10 ml of methanol, and the resulting methanolic solution was admixed with 249 mg (1.011 mmol) of the Boc-ON reagent and then stirred at room temperature for 30 minutes to effect again the reaction of introducing the Boc groups into the 1- and 6′-amino groups of the istamycin B₀ compound. After the reaction, the reaction solution was mixed with 0.2 ml of aqueous NH₄OH and then stirred for 10 minutes, followed by concentration under reduced pressure. The residue obtained was dissolved in 30 ml of chloroform, and the solution in chloroform was washed with 15 ml of 1N aqueous NH₄OH and then with 15 ml of water, dried over anhydrous sodium sulfate, filtered and concentrated to dryness. The residue was chromatographed on a column of silica gel (28 g) developed with chloroform-methanol (30:1 to 10:1) as eluent, to give the desired 1,6′-di-N Boc-3-O-demethylistamycin B₀-4,5-carbamate of the formula

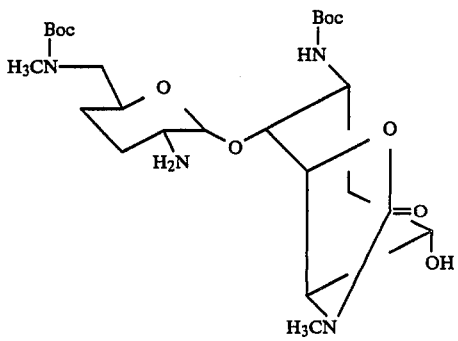

wherein Boc is as defined above, in a yield of 80.3 mg 29.2). $[\alpha]_D^{25}+63.7°$ (c 1, CHCl$_3$).

(e) The 1,6'-di-N-Boc-3-O-demethylistamycin B$_o$-4,5-carbamate obtained (100 mg; 0.148 mmol) was dissolved in 10 ml of methanol, and to the resultant solution was added 81 mg (0.368 mmol) of 3,5-di-t-butyl-o-benzoquinone, followed by agitation at 50° C. for 1 hour. The reaction solution obtained was then admixed with 2 ml of 1M aqueous oxalic acid, stirred at 50° C. for 6 hours and neutralized by addition of powdered sodium hydrogen carbonate (NaHCO$_3$). The neutralized solution was concentrated to dryness and the residue was dissolved in 30 ml of chloroform. The solution in chloroform was washed with water (10ml×3), dried over anhydrous sodium sulfate, filtered and concentrated. The residue was chromatographed on a column of silica gel (10 g) developed with 30 ml of chloroform and subsequently with chloroform-methanol (20:1), to yield 62.5 mg (62.6%) of the desired 2'-deamino-2'-keto-1,6'-di-N-Boc-3-O-demethylistamycin B$_o$-4,5-carbamate of the formula

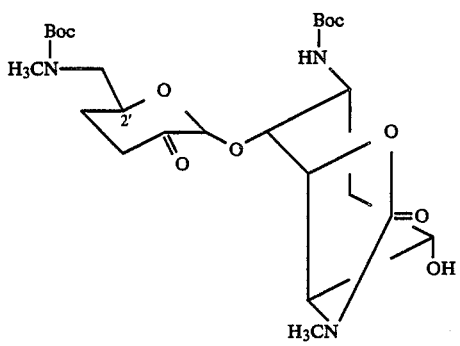

(VI")

wherein Boc denotes t-butoxycarbonyl group. $[\alpha]_D^{28}+52.8°$ (c 1, CHCl$_3$), SIMS: 544 (MH+).

(f) The 2'-deamino-2'-keto derivative of the formula (VI") obtained as above (38.3 mg; 0.0705 mmol) was dissolved in 2 ml of methanol, and the methanolic solution was mixed with 5.3 mg (0.140 mmol) of sodium borohydride (NaBH$_4$) under ice-cooling, followed by agitation for 10 minutes to effect the reductive conversion of the 2'-keto group into the 2'-hydroxy group. The reaction solution obtained was treated by passing a stream of CO$_2$ gas therethrough to consume up the execess of NaBH$_4$, and the solution so treated was concentrated to dryness. The residue was dissolved in 30 ml of chloroform, washed with water (10 ml×3), dried over anhydrous sodium sulfate, filtered and concentrated. The residue obtained was chromatographed on a column of silica gel (6 g) developed with chloroform-methanol (50:1) as eluent, to afford the desired, corresponding 2'-deamino-2'-hydroxy derivative of the formula

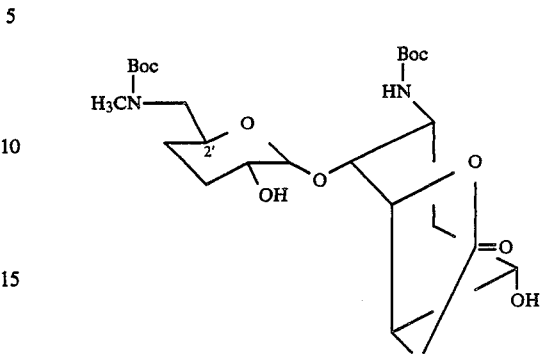

wherein Boc is as defined above, in a yield of 31.5 mg (81.9%). $[\alpha]_D^{28}+52.4°$ (c 1, CHCl$_3$), SIMS: 546 (MH+).

(g) The 2'-deamino-2'-hydroxy derivative of the above formula obtained (30.2 mg; 0.0553 mmol) was dissolved in 5 ml of 50% aqueous dioxane, to which was then added 70 mg (0.222 mmol) of barium hydroxide octahydrate [Ba(OH)$_2$.8H$_2$O], and the resulting mixture was stirred at 70° C. for 6 hours. After the hydrolysis was thus made, the reaction solution was neutralized by passage of a stream of gaseous carbon dioxide (CO$_2$) therethrough and then filtered, and the filtrate was concentrated. The residue was dissolved in 30 ml of chloroform and the solution was washed with water (10 ml×3), dried over anhydrous sodium sulfate, filtered and concentrated to dryness. The residue obtained was then chromatographed on a column of silica gel (3 g) developed with chloroform-methanol-conc. aqueous ammonium hydroxide (120:30:5), to obtain 24.5 mg (85.2%) of 1,6'-di-N-Boc-2'-deamino-2'-hydroxy-3-O-demethylistamycin B$_o$ of the formula

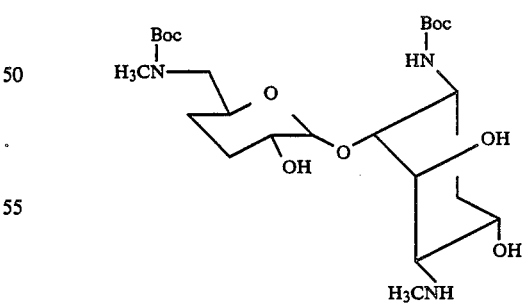

wherein Boc is as defined above. $[\alpha]_D^{18}+77.0°$ (c 1, CHCl$_3$). SIMS: 520 (MH+).

(h) The product compound obtained in the above procedure (g) (23.5 mg; 0.0452 mmol) was dissolved in 5 ml of dioxane, and the resulting solution was mixed with 18.5 mg (0.0678 mmol) of N hydroxysuccinimide ester of N-Boc-glycine represented by the formula

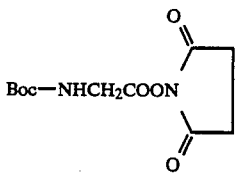

wherein Boc is t-butoxycarbonyl group and also with 15 μl (0.108 mmol) of triethylamine. The resulting mixture was stirred at 60° C. for 1 hour to effect the acylation of the 4-methylamino group of the istamycin $B_o$ compound with the glycine compound. The reaction solution obtained was then mixed with 0.1 ml of 1N aqueous $NH_4OH$ and then stirred at room temperature for 10 minutes, followed by concentration to dryness. The residue was dissolved in 30 ml of chloroform and the solution was washed with water (10 ml×3), dried over anhydrous sodium sulfate, filtered and concentrated. The residue was then chromatographed by preparative thin layer chromatography (PLC) (0.5 mm×1, developed with chloroform-methanol (10:1)), to obtain the desired 1,6',2''-tri-N-t-butoxycarbonyl-2'-deamino-2'-hydroxy-3-O-demethylistamycin B represented by the formula

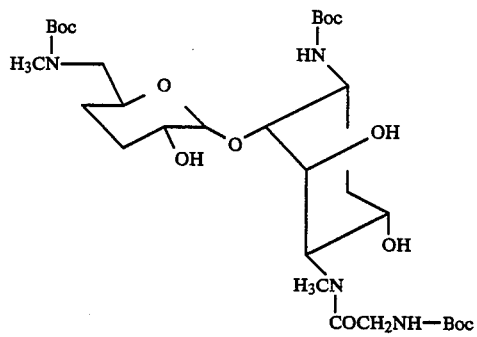

wherein Boc is as defined above, in a yield of 26.9 mg (87.9%). $[\alpha]_D^{20}+77.7°$ (c 1, $CHCl_3$), SIMS: 677 (MH+).

(i) The tri-N-Boc derivative of the formula (Ib) obtained in the above procedure (h) (25.5 mg; 0.0377 mmol) was added into 90% aqueous trifluoroacetic acid, and the resulting mixture was allowed to stand at room temperature for 1 hour to effect the hydrolytic removal of the Boc groups. The reaction solution as formed was concentrated to dryness and the residue was taken up into 3 ml of water, to which 1N aqueous $NH_4OH$ was then added to adjust to pH 6–7. The resulting aqueous solution neutralized was then passed into a column of 3 ml of Amberlite CG-50 ($NH_4^+$-form) to make the adsorption of the deprotected product by the Amberlite resin. The resin column was washed with 10 ml of water, then with 10 ml of 0.1N aqueous $NH_4OH$ and finally with 10 ml of 0.2N aqueous $NH_4OH$ and was subsequently eluted with 10 ml of 0.3N aqueous $NH_4OH$. The fractions of the eluate containing the desired product was concentrated to dryness, affording 12.8 mg (90.2%) of the desired Compound No. 2 of this invention, that is, 2'-deamino-2'-hydroxy-3-O-demethylistamycin B. $[\alpha]_D^{23}+109.4°$ (c 1, water).

EXAMPLE 3

PRODUCTION OF COMPOUND NO. 3 OF THIS INVENTION (a) To a solution of 66 mg (0.349 mmol) of N-t-butoxycarbonyl-β-alanine in 3 ml of acetonitrile were added 90 mg (0.351 mmol) of DSC (N,N'-disuccinimidyl carbonate) and 30 μl (0.372 mmol) of pyridine, and the resulting mixture was stirred at 40° C. for 3 hours, to prepare an active ester of the N-Boc-β-alanine. Into the reaction solution as formed were added 46.5 mg (0.0871 mmol) of 1,6'-di-N-Boc-2'-deamino-2'-hydroxyistamycin $B_o$, an intermediate product of the formula (V') as prepared in the Example 1 (g) given hereinbefore and 50 μl (0.359 mmol) of triethylamine. The mixture obtained was stirred at 50° C. for 15 hours, admixed with 0.4 ml of 1N aqueous $NH_4OH$ and then stirred for 10 minutes. The resulting reaction solution was concentrated to dryness and the residue was dissolved in 50 ml of chloroform. The solution in chloroform was washed with water (20 ml×3). dried over anhydrous sodium sulfate, filtered and concentrated. The residue obtained was purified by chromatographying on a column of silica gel (5 g) developed with chloroform-methanol (30:1), to afford the desired 4-N-(3''-N-Boc-β-alanyl)-1,6'-di-N-Boc-2'-deamino-2'-hydroxyistamycin B of the formula

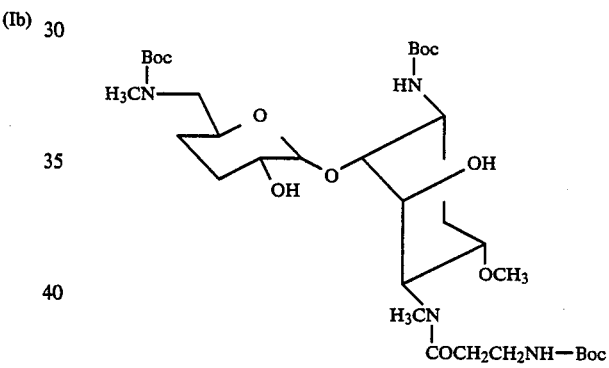

wherein Boc is t-butoxycarbonyl group, in a yield of 53.2 mg (86.6%). $[\alpha]_D^{28}+77.0°$ (c 1, $CHCl_3$).

(b) The 4-N-(3''-N-Boc-β-alanyl) derivative of the above formula obtained in the procedure (a) (30.9 mg; 0.0438 mmol) was admixed with 90% aqueous trifluoroacetic acid, and the mixture was allowed to stand at room temperature for 1 hour to effect the hydrolytic removal of the Boc groups. The reaction solution was concentrated to dryness and the residue was dissolved in 2 ml of water, to which was then added 1N aqueous $NH_4OH$ to adjust to pH 6–7. The aqueous solution neutralized was passed into á column of 4 ml of Amberlite CG-50 ($NH_4^+$-form) to make the adsorption of the deprotected product by the Amberlite resin. The resin column was washed with 12 ml of water and then successively with 10 ml portions of 0.1N aqueous $NH_{40}H$, 0.2N aqueous $NH_4OH$ and 0.3N aqueous $NH_4OH$ and was subsequently eluted with 10 ml of 0.4N aqueous $NH_4OH$. The fractions of the eluate containing the desired product were combined together and concentrated to dryness, affording 16.9 mg (95.5%) of the desired Compound No. 3 of this invention, namely 4-N-(β-alanyl)-2'-deamino-2'-hydroxyistamycin $B_o$. $[\alpha]_D^{25}+119.6°$ (c 1, water).

EXAMPLE 4

PRODUCTION OF COMPOUND NO. 4 OF THIS INVENTION (a) To a solution of 21 mg (0.111 mmol) of N-Boc-β-alanine in 3 ml of acetonitrile were added 29 mg (0.113 mmol) of DSC and 10 μl (0.124 mmol) of pyridine, followed by agitation of the resulting mixture at 50° C. for 2 hours to prepare an active ester of the N-Boc-β-alanine. Into the reaction solution as formed were added 20 μl (0.143 mmol) of triethylamine and 29.0 mg (0.0558 mmol) of 1,6-di-N-Boc-2'-deamino-2'-hydroxy-3-O-demethylistamycin $B_o$, an intermediate product as prepared in the Example 2(g) hereinbefore. The mixture obtained was stirred at 50° C. for 2 hours and then admixed with 0.2 ml of 1N aqueous $NH_4OH$, followed by agitation for 10 minutes. The reaction solution obtained was concentrated to dryness and the residue was dissolved in 30 ml of chloroform. The solution in chloroform was washed with water (10 ml×3), dried over anhydrous sodium sulfate, filtered and concentrated. The residue was purified by chromatographying on a column of silica gel (5 g) developed with chloroform-methanol (15:1), and there was obtained 33.5 mg (86.9%) of the desired 4N-(3''-N-Boc-β-alanyl)-1,6'-di-N-Boc-2'-deamino-'-hydroxy-3-O-demethylistamycin $B_o$. $[\alpha]_D^{27} +87.4°$ (c 1, $CHCl_3$).

(b) The 4-N-(3''-N-Boc-β-alanyl) derivative obtained in the above procedure (a) (32.0 mg; 0.0463 mmol) was admixed with 90% aqueous trifluoroacetic acid, and the mixture was allowed to stand at room temperature for 1 hour to effect the removal of the Boc groups. The resulting reaction solution was concentrated to dryness and the residue was dissolved in 1 ml of water, to which was then added 1N aqueous $NH_4OH$ to adjust to pH 6–7. The aqueous solution so obtained was passed into a column of 3 ml of Amberlite CG-50 ($NH_4^+$-form) to make the deprotected product adsorbed by the Amberlite resin. The resin column was then washed with 10 ml of water and with 10 ml of 0.3N aqueous $NH_4OH$ and subsequently eluted with 10 ml of 0.4N aqueous $NH_4OH$. The fractions of the eluate containing the desired product were combined together and concentrated to dryness to yield 16.3 mg of the desired Compound No. 4 of this invention, namely 4-N-(β-alanyl)-2'-deamino-2'-hydroxy-3-O-demethylistamycin $B_o$. $[\alpha]_D^{23} +109.4°$ (c 1, water).

I claim:

1. A 2'-deamino-2'-hydroxyistamycin $B_o$ derivative represented by the formula (I)

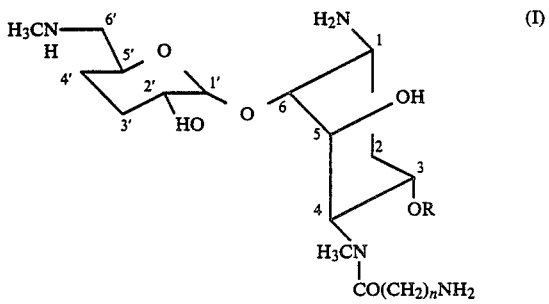

wherein R is a methyl group or a hydrogen atom and n is an integer of 1 or 2, and a pharmaceutically acceptable acid addition salt thereof.

2. A compound as claimed in claim 1 which is 2'-deamino-2'-hydroxyistamycin B, namely a compound of the formula (I) where R is a methyl group and n is 1.

3. A compound as claimed in claim 1 which is 2'-deamino-2'-hydroxy-3-O-demethylistamycin B, namely a compound of the formula (I) where R is a hydrogen atom and n is 1.

4. A compound as claimed in claim 1 which is 4-N-(β-alanyl)-2'-deamino-2'-hydroxyistamycin $B_o$, namely a compound of the formula (I) where R is a methyl group and n is 2.

5. A compound as claimed in claim 1 which is 4-N-(β-alanyl)-2'-deamino-2'-hydroxy-3-O-demethylistamycin $B_o$, namely a compound of the formula (I) where R is a hydrogen atom and n is 2.

6. A pharmaceutical composition comprising a bactericidally effective amount of the compound of the formula (I) as defined in claim 1 or a pharmaceutically acceptable acid addition salt thereof, as the active ingredient, in combination with a pharmaceutically acceptable carrier for the active ingredient.

7. A method of treating bacterial growth in an animal or human which comprises administering a bactericidally effective amount of the compound of the formula (I) as defined in claim 1 or a pharmaceutically acceptable acid addition salt thereof to an animal infected with or susceptible to bacteria.

8. A compound which is selected from 2'-deamino-2'keto-1,6'-di-N-t-butoxycarbonyl-istamycin $B_o$-4,5-2'-deamino-2'-keto-1,6'-di-N-t-butoxycarbonyl-3-O-demethylistamycin $B_o$-4,5-carbamate.

* * * * *